United States Patent [19]

Wright

[11] 4,219,055
[45] Aug. 26, 1980

[54] SYRINGE FILLING AID

[76] Inventor: George R. Wright, 202 S. 11th St., Lincoln, Nebr. 68508

[21] Appl. No.: 761,490

[22] Filed: Jan. 21, 1977

Related U.S. Application Data

[63] Continuation of Ser. No. 589,612, Jun. 23, 1975, abandoned.

[51] Int. Cl.² ............................ B65B 3/32; B67C 3/16
[52] U.S. Cl. ................................ 141/27; 141/330; 141/375; 128/218 D
[58] Field of Search .................. 141/37 S, 2, 18–27, 141/1, 29, 250, 266, 284, 279, 329, 330, 311, 368, 231–233; 128/218 D; 222/309; 403/104; 128/272

[56] References Cited

U.S. PATENT DOCUMENTS

| 400,033 | 3/1889 | Alliger | 403/104 |
| 3,610,241 | 10/1971 | Lemarie | 128/272 |
| 3,807,464 | 4/1974 | Putesky | 141/37 S |
| 3,833,030 | 9/1974 | Waldbauer | 141/37 S |
| 3,853,158 | 12/1974 | Whitty | 141/37 S |
| 3,875,979 | 4/1975 | Hults | 141/37 S |

*Primary Examiner*—Houston S. Bell, Jr.
*Attorney, Agent, or Firm*—Hiram A. Sturges

[57] ABSTRACT

A syringe filling aid comprising a body having bottle holding means at one end and a hilt engaging portion at the other end for engaging the hilt of a syringe when the needle of the syringe is in the bottle, the hilt engaging portion having a notch in which the syringe can be rested, and a plunger stop assembly adjustably fixable to the body for limiting movement of the plunger to a predetermined dose setting.

9 Claims, 4 Drawing Figures

SYRINGE FILLING AID

This is a continuation of application Ser. No. 589,612, filed June 23, 1975 now abandoned.

FIELD OF THE INVENTION

This invention is in the field of aids for facilitating the filling of syringes with medicine.

DESCRIPTION OF THE PRIOR ART

Heretofore there has not been available in the drugstores, to my knowledge, any device for facilitating the loading of syringes with medicine. More particularly there has not been a device adapted to hold the medicine bottle, and also to hold the syringe in place with respect to the bottle while the plunger is pulled out to the desired precise amount.

This is particularly a problem for diabetics who must take insulin shots. Accuracy of dosage is relatively easy for the alert and dexterous, but many of the users are handicapped because of being tired, or are not naturally dexterous.

Persons with poor vision, such as the elderly, have a particular problem and also the blind and children.

Beginners who have not taken shots before tend to have a great amount of fear. First of all they fear the whole concept of shots. Some fear to start the process of shots for fear they will never be able to stop it and that the best way is never to start. Of course, this is not rational because insulin can be extremely vital to a diabetic, for example. However, rationality is not always present and it is a particular need for the public to have available an aid to the filling of syringes which makes accuracy easily attainable throughout repeated doses.

The tired, the blind, the clumsy and children could benefit from having also the feature of a syringe receiving support cradle to hold the needle away from contaminating surfaces so that the syringe can be rested safely after loading and while preparing a portion of the body to receive a shot.

SUMMARY OF THE INVENTION

A syringe filling system comprising a syringe for use with a syringe of the type having an elongated tube with a needle at one end and a hilt at its other end, the hilt extending transeversly of the tube and having a plunger telescopingly projecting through the hilt and the tube, and a syringe filling aid comprising a body having a bottle holding means thereon preferably in the form of resilient jaws for securing a medicine bottle to the body, a hilt-engaging portion attached to the body and spaced in one direction from the bottle holding means and adapted to engage that side of the hilt which is opposite to the needle end of the tube so as to limit movement of the tube away from the bottle when the needle is in the bottle, is a main combination of the invention.

A further feature of importance is having the body rounded so that as a person grips around the bottle and the body, the body will be comfortable in the hand.

Still another object is to provide feet on the body or other suitable means so as to cause the body to rest with stability right side up on a floor.

Another object of the invention is to provide a notch on the outer end of the hilt-engaging means for providing a syringe receiving cradle to support the needle so as to keep it away from contaminating surfaces and sterile.

A still further object of the invention is to provide a plunger stop assembly having a stop disposed on the other side of the hilt-engaging means from the bottle holding means and adjustably attached to the body so as to be fixable in any desired position for stopping the plunger at the precise place for corresponding to a preselected dosage.

DESCRIPTION OF THE PREFERRED EMBODIMENT

Figure 1:
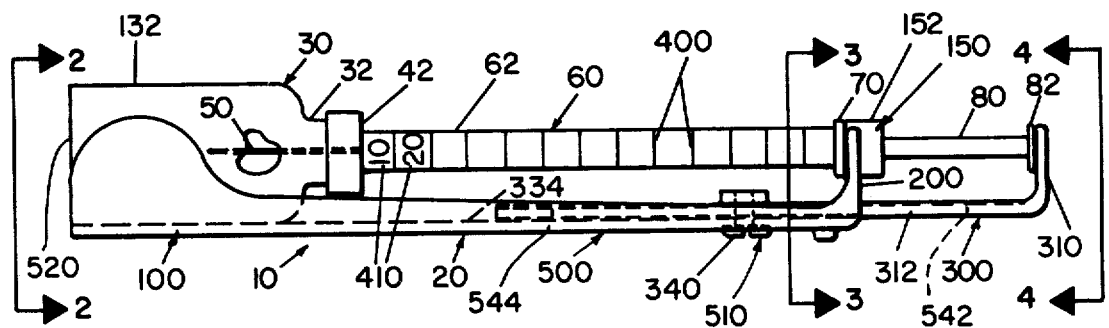
FIG. 1 is a side elevation of the fringe filling aid of this invention shown with a medicine bottle and syringe mounted therein, dotted lines indicating the position of an elongated stop extension.
Figure 3:
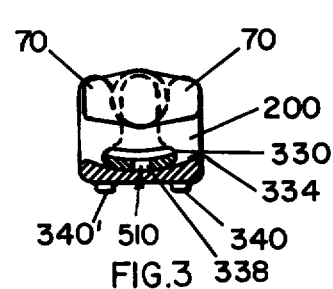
FIG. 3 is a sectional view of FIG. 1 as seen along the line 3—3.

A syringe filling assembly or system is generally indicated at 10 in FIG. 1 and comprises a syringe filling aid, generally indicated at 20, which latter is adapted to hold a medicine bottle 30, having a neck 32, having a penetrable cover 42, which is adapted to be pierced by the needle 50 of a syringe, generally indicated at 60, which latter has a tubular portion 62 in the forward end of which the needle 50 is mounted in a conventional manner, not shown, and with the needle at one end of the syringe tube 62, a hilt 70 is attached to the tube at its other end and extends transveresly of the tube 62 projecting from the sides thereof, as best seen in FIG. 3.

The tube 62 has a plunger telescopingly projecting through the hilt end thereof as seen at 80, the plunger having a handle 82 transveresely disposed with respect to its elongation, which latter is parallel to the tube 62, the handle 82 being fixed to the plunger 80 and being adapted to be gripped between the thumb and finger during pulling of the plunger outwardly.

The syringe filling aid 20 has a body 100 which is elongated in the same direction as the syringe 60 and parallel thereto, the body 100 has a body holding assembly, generally at 120, at one end thereof which can be called the forward end, and the bottle holding means 120 preferably comprises two spaced jaws 126, which preferably have inner and outer surfaces 128 and 129, which latter are of the shape of portions of cylinders, one such cylinder being of substantially the shape and size of the cylindrical outer portion 132 of the bottle 30 at times when the bottle is in place. It will be understood that the jaws 126 are resilient and that their normal position would be closer together than the position shown in FIG. 2 when they engage the bottle 30 so that when the bottle is in place, it is gripped between the jaws 126 because of the resilence.

The jaws 126 are spaced apart at their upper ends.

A hilt-engaging portion 200 is disposed on the body 100 and is preferably of one piece therewith as also are the jaws 126.

The hilt-engaging portion 200 is at the rearward end of the body 100, and therefore spaced in one direction from the bottle holding assembly 120 and is adapted to engage that side of the hilt 70 which is opposite the needle end of the syringe, whereby the hilt-engaging portion 200 limits movement of the tube 62 away from the bottle 30 when the needle 50 is in the bottle and when an enlarged annular end cap 150 of the syringe has its cylindrical outer surface cradled in a notch 170 in the hilt-engaging portion 200, since the cylindrical outer surface 152 of the cap 150 is conventionally coaxial with the cylindrical tube 62.

The syringe filling aid 20 further has a plunger stop assembly, generally indicated at 300, which comprises a stop 310 disposed on the other or rearward side of the hilt-engaging member 200 from the bottle holding assembly 120.

The plunger stop assembly 300 further has a stop extension 312 which telescopes with respect to the body 100 and which extends through an opening 330 in the hilt-engaging portion 200, whereby the extension 312 can lie along the upper side of the body 100, since the upper side of the majority of the body 100 is normally substantially horizontal and elongated in the same direction as the tube 62, the upper side of the body being seen at 334 in FIG. 3.

The stop extension 312 is provided with a longitudinal slot 338, receiving therethrough a nut and bolt assembly 340, which latter connects it to the body 100 in an adjustable fashion.

Suitable support means or feet are provided at the rearward end of the body 100 so as to tend to hold the body from rocking when resting on a flat surface, as it otherwise might because of the presence of the rounded outer surfaces of the body at its bottle end and because of the downward projection slightly of a portion of bolt and nut assembly 340.

At least the majority of the hilt-engaging portion 200, and of the bottle holding assembly 120 are disposed on the same side of the body 100, namely the upper side. That half of the elongated body which is nearest to the bottle holding assembly 120 can be seen to have a generally smooth and gradually curved convex outer surface extending across the majority of that side of the said half which is opposite to the side thereof on which the hilt-engaging portion 200 is primarily disposed. For that reason the body is round at its forward end on its underside and so the feet 340 are important.

Figure 2:
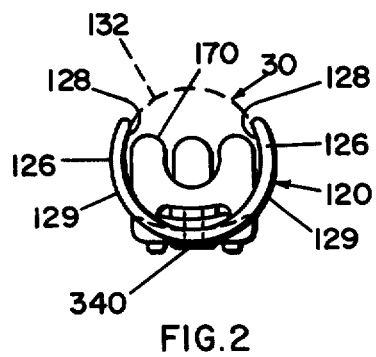
FIG. 2 is a view of FIG. 1 as seen along the line 2—2.

As best seen in FIG. 2 a bottle holding assembly 120 and that part of the elongated body 100 which is nearest to the bottle holding assembly 120 together substantially provide the syringe filling assembly or syringe filling aid 10 with a gradually curved convex outer surface 129, as seen in FIG. 2, which latter is substantially in the shape of a portion of the cylinder. The substantially cylindrical surface 129 cooperates with the cylindrical exterior of the bottle 132 where it is exposed between the jaws 126 for providing in total a substantially complete exterior surface of cylindrical shape.

Figure 4:
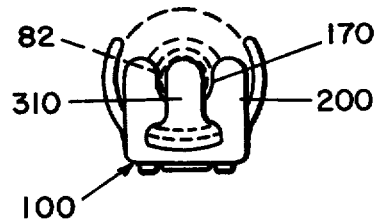
FIG. 4 is a view of FIG. 1 as seen along the line 4—4.

The stop 310 is preferably of a size from right to left at its upper end which is lesser than the side from right to left of the cylindrical handle 82 of the plunger 80, so that the plunger can be gripped at the sides of the stop 310, and as best seen in FIG. 4.

In FIG. 1, it can be seen that the tube 62 is provided with indicia 400, normally bearing numbers, two samples of which can be seen at 410 so as to gauge the amount of the dosage in a conventional manner.

In operation it will be seen that setting the stop 310 in fixed position corresponding to a desired dosage will insure that it will give the same dosage in all following uses without close observation by simply drawing the plunger out to the stop.

If the dosage should change by prescription, then the stop can be put in a new position and fixed.

After the syringe is filled it is simply moved up out of the notch 170, the needle withdrawn from the bottle and used. If desired, after it has been removed, and at a time when the body 100 is rested on the floor, or a table top, the tube 62 can be placed at an acute angle to the body and rested in the notch 170, so as to support the needle in a safe place from contamination.

The body 100 and the stop extension 12 together define two parts of a length adjustment assembly 500, the said two parts lapping each other, as best seen in FIG. 1, and telescoping with respect to each other in directions generally toward and away from the bottle-holding assembly 120, the said telescoping movements being in the area between the hilt-engaging portion 200 and the bottle-holding assembly 120.

A telescopically attaching assembly is generally shown at 510 and attaches the two parts of the attachment assembly 500 together, the two parts being the body 100 and the stop extension 312, the said telescopic assembly 510 comprising, as one of its elements, the bolt and nut assembly 340.

The cylindrical outer portion 132 of the bottle 30 is larger than the neck 32 and can be defined as a larger portion of the bottle, which latter is adjacent the base end 520 of the bottle. It is against the outer cylindrical larger portion 132 of the bottle that the resilient jaws 126 press, and it will be understood that since the jaws 126 are resilient, the bottle 30 can be manually moved with respect to the jaws 126 and, therefore, with respect to the bottle-holding assembly 120 in general.

As best seen in FIG. 1, there is no impediment in the way of movement of the bottle, for example, from a flush position in which the base end 520 of the bottle is flush with the adjacent end of the body 100 to another position closer to the hilt-engaging portion 200, a substantial movement from a flush position toward the hilt-engaging portion 200 being possible while the bottle 30 is yet in the grip of the jaws 126 and held thereby.

The pentratable cover 42 of the bottle 30 defines a needle-receiving end of the bottle 30.

As above described, there is a length adjustable assembly 500 comprising the body 100 and the stop extension 312 as the two parts thereof, and it will be seen that at least one of the parts of the length adjustable assembly 500 has an elongated slot therethrough having openings facing upwardly and downwardly, the slot being seen at 338 in FIG. 3.

That one of the openings of the slot 338 which faces downward in FIG. 3 can be seen to be facing the opposite one of the two parts of the adjustment assembly 500, the opposite part being seen in FIG. 3 to be the body 100.

As best seen in FIG. 1, the slot can extend from a first end which is adjacent to the stop 310 to an opposite end 544 which is farthest from the stop 310, whereby the slot 338 can have a substantial length. It is, therefore, possible for at least one-third of the slot 338 to be disposed, or in a sense, being disposable, on the bottle of the bottle-holding assembly 120 side of the hilt-engaging portion 200.

As thus described an injection aid is believed to be provided of great value which provides handiness, accuracy and simplicity.

I claim:

1. A syringe filling aid for filling a syringe of the type having an elongated tube having a needle at one end and a hilt at its other end, said hilt extending transversely of said tube, said tube having a plunger telescopically projecting through the hilt end of said tube, said aid comprising: an elongated body, a bottle-holding means attached to said body for securing a bottle of medicine to said body, a hilt-engaging portion attached to said body and spaced in one direction from said bottle-holding means and adapted to engage that side of said hilt which is opposite the needle end of said syringe tube to limit movement of said syringe tube away from said bottle-holding means when said needle is in said bottle, a plunger stop assembly comprising a stop disposed on the other side of said hilt-engaging means from said bottle-holding means and a stop extension, said body and said stop extension defining two parts of a length adjustment assembly, said two parts lapping each other and telescoping with respect to each other in directions generally toward and away from said bottle-holding means, the majority of said lapping of said two parts being in the area between said hilt-engaging means and said bottle-holding means, means telescopically attaching said two parts of said attachment assembly together, and means for attaching said stop extension adjustably to said body in a manner so that said stop can be fixed in any one of many positions of distance from said hilt-engaging means.

2. The syringe filling aid of claim 1 having a notch in the outer end of said hilt-engaging means for receiving said syringe to support the needle end of said syringe for sterility.

3. The syringe filling aid of claim 1 having said telescopic extension attaching means comprising a slot in said extension generally parallel to said elongated body, and a bolt and nut assembly extending through said body and through said slot.

4. The syring filling aid of claim 1 in which said hilt-engaging means has an opening therethrough through which said stop extension can slide.

5. The syringe filling aid of claim 1 in which said body has means on its underside adapted to hold it upright on a level surface with stability.

6. A syringe filling system comprising a syringe filling aid as described in claim 1 having a bottle in said bottle-holding means, said bottle having a base end and a needle-receiving end and having a larger portion of larger exterior size nearer its base end, said bottle-holding means comprising two resilient body-holding portions attached to said body and pressing against opposite sides of said larger portion of said bottle and slidably receiving said bottle therebetween in a manner permitting said bottle to slide toward and away from said hilt-engaging means, said body and said bottle-holding means being free of impediment to movement of said bottle with respect to said holder and toward said hilt-engaging portion from a flush position of said bottle in which latter the base of said bottle is flush with that portion of said holder which latter is farthest from said hilt-engaging portion through a substantial movement distance.

7. The syringe filling aid of claim 1 having at least one of the parts of said length adjustable assembly having an elongated slot therethrough having openings, said slot defining a part of said telescopic attachment means, one of the openings of said slot facing the opposite one of said two parts of said adjustment assembly, at least one-third of said slot being disposable on the bottle-holding means side of said hilt-engaging means.

8. The syringe filling aid of claim 1 in which said stop extension attaching means is located between said hilt-engaging means and said bottle-holding means.

9. The syringe filling aid of claim 1, the majority of said hilt-engaging portion and of said bottle holding means being disposed on a same side of said body, said bottle holding means and that part of said elongated body which is nearest to said bottle holding means together providing said aid with a gradually curved convex outer surface.

* * * * *